US009867013B2

United States Patent
Nakata et al.

(10) Patent No.: US 9,867,013 B2
(45) Date of Patent: *Jan. 9, 2018

(54) METHOD AND SYSTEM FOR DETERMINING OBJECT MOTION BY CAPTURING MOTION DATA VIA RADIO FREQUENCY PHASE AND DIRECTION OF ARRIVAL DETECTION

(71) Applicant: OAHU GROUP, LLC, Honolulu, HI (US)

(72) Inventors: Robert Haruo Nakata, Honolulu, HI (US); Isar Mostafanezhad, Honolulu, HI (US); Robert Jeffrey Nakata, Honolulu, HI (US)

(73) Assignee: Oahu Group, LLC, Honolulu, HI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/351,395

(22) Filed: Nov. 14, 2016

(65) Prior Publication Data

US 2017/0156035 A1 Jun. 1, 2017

Related U.S. Application Data

(63) Continuation of application No. 14/976,511, filed on Dec. 21, 2015, now Pat. No. 9,497,597, which is a continuation of application No. 14/517,749, filed on Oct. 17, 2014, now Pat. No. 9,219,993.

(60) Provisional application No. 61/893,222, filed on Oct. 20, 2013.

(51) Int. Cl.
*H04L 27/08* (2006.01)
*H04W 4/02* (2009.01)
*H04B 1/3827* (2015.01)

(52) U.S. Cl.
CPC ............ *H04W 4/026* (2013.01); *H04B 1/385* (2013.01); *H04W 4/027* (2013.01)

(58) Field of Classification Search
CPC ....... H04W 4/026; H04W 4/027; H04B 1/385
See application file for complete search history.

(56) References Cited

U.S. PATENT DOCUMENTS

| 6,324,296 | B1 * | 11/2001 | McSheery | G06T 7/80 |
| | | | | 250/203.3 |
| 8,948,839 | B1 * | 2/2015 | Longinotti-Buitoni | A61B 5/6804 |
| | | | | 29/825 |
| 9,380,531 | B1 * | 6/2016 | Subramanian | H04W 52/0216 |
| 9,384,587 | B2 * | 7/2016 | Davison | G06T 17/00 |
| 9,389,303 | B2 * | 7/2016 | Ben Hamida | G01S 5/0215 |
| 9,489,820 | B1 * | 11/2016 | Kusens | A61B 5/746 |
| 9,519,969 | B1 * | 12/2016 | Kusens | G06T 7/73 |
| 9,706,489 | B2 * | 7/2017 | Subramanian | H04W 52/02 |
| 9,741,227 | B1 * | 8/2017 | Kusens | G08B 21/043 |

(Continued)

*Primary Examiner* — Erin File
(74) *Attorney, Agent, or Firm* — Jeremy Forest

(57) ABSTRACT

Methods and systems for determining the motion of an object by capturing motion data. The methods and systems may comprise the use of motion sensor tags adapted for disposal on an object, wherein motion data may be collected by said motion sensor tags and transmitted via radio frequency signal for processing of collected data comprising the motion data, direction of arrival data, amplitude data, and phase data. The same system may also be adapted to determine the position of a UAV or aircraft by intercepting radio frequency communications signals emanating from the object.

21 Claims, 7 Drawing Sheets

(56) References Cited

U.S. PATENT DOCUMENTS

| | | | |
|---|---|---|---|
| 2006/0204045 A1* | 9/2006 | Antonucci | G06K 9/00342 382/107 |
| 2007/0035562 A1* | 2/2007 | Azuma | G03B 13/28 345/633 |
| 2008/0238770 A1* | 10/2008 | Rofougaran | G01C 21/20 342/357.32 |
| 2008/0242349 A1* | 10/2008 | Rofougaran | H04M 1/72572 455/556.1 |
| 2008/0267150 A1* | 10/2008 | Rofougaran | G01S 19/49 370/338 |
| 2009/0111670 A1* | 4/2009 | Williams | A63B 23/0464 482/146 |
| 2009/0258703 A1* | 10/2009 | Brunstetter | A63F 13/12 463/36 |
| 2010/0004860 A1* | 1/2010 | Chernoguz | G01C 22/006 701/494 |
| 2010/0004896 A1* | 1/2010 | Yen | A63F 13/06 702/153 |
| 2010/0185093 A1* | 7/2010 | Hamilton | A61B 8/483 600/443 |
| 2010/0214216 A1* | 8/2010 | Nasiri | A63F 13/06 345/158 |
| 2010/0253700 A1* | 10/2010 | Bergeron | G03B 35/00 345/633 |
| 2010/0304931 A1* | 12/2010 | Stumpf | A63B 22/02 482/4 |
| 2011/0134220 A1* | 6/2011 | Barbour | H04N 13/0207 348/44 |
| 2011/0227825 A1* | 9/2011 | Liberty | G06F 3/0383 345/158 |
| 2011/0228098 A1* | 9/2011 | Lamb | G01S 17/023 348/164 |
| 2012/0133638 A1* | 5/2012 | Davison | G06T 17/00 345/419 |
| 2012/0307084 A1* | 12/2012 | Mantzel | H04N 5/23248 348/208.2 |
| 2012/0307085 A1* | 12/2012 | Mantzel | H04N 5/2329 348/208.4 |
| 2013/0041291 A1* | 2/2013 | Soubeyrat | A61B 5/1038 600/595 |
| 2013/0127980 A1* | 5/2013 | Haddick | G06F 3/013 348/14.08 |
| 2013/0159350 A1* | 6/2013 | Sankar | G06F 3/011 707/784 |
| 2013/0278631 A1* | 10/2013 | Border | G02B 27/017 345/633 |
| 2014/0083058 A1* | 3/2014 | Issing | B65G 1/1378 53/473 |
| 2014/0206442 A1* | 7/2014 | Hollander | G07F 17/3206 463/31 |
| 2015/0119073 A1* | 4/2015 | Nakata | H04W 4/026 455/456.1 |
| 2015/0126799 A1* | 5/2015 | Vahala | A61N 5/1049 600/1 |
| 2016/0219517 A1* | 7/2016 | Ylamurto | H04W 52/0219 |

* cited by examiner

- Antenna array is located at the origin with array boresight along x axis
- Tags are located at positions 1, 2, 3

- Antenna array is located at the origin with array boresight along x axis
- Tags are located at positions 1, 2, 3

METHOD AND SYSTEM FOR DETERMINING OBJECT MOTION BY CAPTURING MOTION DATA VIA RADIO FREQUENCY PHASE AND DIRECTION OF ARRIVAL DETECTION

CROSS-REFERENCE TO RELATED APPLICATIONS

This application claims the benefit under 35 U.S.C. §119 (e) of U.S. Provisional Patent Application No. 61/893,222, filed Oct. 20, 2013, which is incorporated herein by reference in its entirety for all purposes.

FIELD

The present disclosure generally relates to methods and systems for determining the motion of an object via the collection and processing of motion data. In certain embodiments, the methods and systems comprise the use of motion sensor tags disposed on an object, wherein motion data is collected by said motion sensor tags and transmitted via radio frequency signal for processing of a collected data set, said collected data set comprising the motion data, direction of arrival data, amplitude data, and phase data.

BACKGROUND

Known methods of motion capture may include camera-type systems, wherein reflective markers attached to the body are observed by a number of cameras from which the 3D position can be reconstructed using triangulation of each camera 2D image. On the other hand, magnetic-type trackers measure the field as emitted by a source placed near the subject from which position, orientation, acceleration, and/or velocity of the sensor with respect to the source can be calculated. Other systems include the use of inertial measurement units (IMUs) or goniometers disposed on a body that capture position, orientation, acceleration, and/or velocity data of the body in a three-dimensional space. However, such systems commonly suffer from drift and noise errors that affect the accuracy of the motion data being processed. While some methods implement the use of predetermined kinetic calculations and/or predetermined data generated by contact of the body with the external world, such methods of updating the motion data still suffer from inaccuracies due to the fact that they are relying on limitations that are not generated by the motion sensors themselves, or are not generated in real time. Accordingly, there remains a need to develop motion sensor methods and systems that have the ability to more accurately capture the three-dimensional position, orientation, acceleration, and/or velocity of the object.

SUMMARY

Described herein are systems and methods for capturing the motion of an object in a three-dimensional space. In certain embodiments, the method comprises:
collecting motion data from a plurality of motion sensor tags disposed on an object;
transmitting the motion data via at least one radio frequency signal;
receiving the motion data, wherein receiving the motion data further provides direction of arrival data, amplitude data, and phase data from the radio frequency signal; and
processing a collected data set comprising the motion data, the direction of arrival data, the amplitude data, and the phase data, wherein said processing provides three-dimensional data comprising a position, an orientation, an acceleration, and/or a velocity of the object in a three-dimensional space.

In certain embodiments, the system comprises:
a plurality of motion sensor tags adapted to collect motion data from an object;
at least one radio frequency transmitter adapted to transmit the motion data via a radio frequency signal;
at least one receiving antenna adapted to receive the motion data from the radio frequency signal, and derive direction of arrival data, amplitude data, and phase data via receipt of the radio frequency signal; and
at least one signal processor adapted to provide three-dimensional data comprising a position, an orientation, an acceleration, and/or a velocity of the object in a three-dimensional space by processing a collected data set comprising the motion data, the direction of arrival data, the amplitude data, and the phase data.

Also described herein are systems and methods for monitoring the motion of a target platform, wherein said target platform implements the use of radio frequency transmissions. In certain embodiments, the method comprises:
intercepting motion data of a target platform via a radio frequency transmission generated by said target platform, wherein receiving the motion data via the radio frequency transmission further provides direction of arrival data, amplitude data, and phase data from the radio frequency transmission; and
processing a collected data set comprising the motion data, the direction of arrival data, the amplitude data, and the phase data, wherein said processing provides three-dimensional data comprising a position, an orientation, an acceleration, and/or a velocity of the target platform in a three-dimensional space.

DETAILED DESCRIPTION

Figure 1:
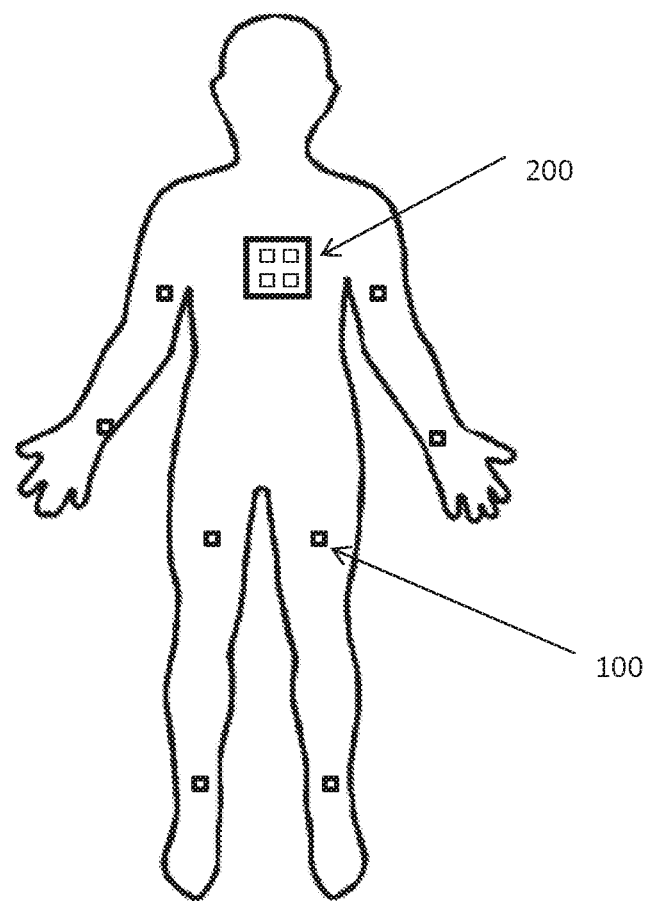
FIG. 1 provides a front view of an exemplary motion sensor system.

Described herein are systems and methods for capturing the motion of an object in a three-dimensional space. In certain embodiments, the method comprises:

collecting motion data from a plurality of motion sensor tags disposed on an object;

transmitting the motion data via at least one radio frequency signal;

receiving the motion data, wherein receiving the motion data further provides direction of arrival data, amplitude data, and phase data from the radio frequency signal; and processing a collected data set comprising the motion data, the direction of arrival data, the amplitude data, and the phase data, wherein said processing provides three-dimensional data comprising a position, an orientation, an acceleration, and/or a velocity of the object in a three-dimensional space.

In certain embodiments, the system comprises:

a plurality of motion sensor tags adapted to collect motion data from an object;

at least one radio frequency transmitter adapted to transmit the motion data via a radio frequency signal;

at least one receiving antenna adapted to receive the motion data from the radio frequency signal, and derive direction of arrival data, amplitude data, and phase data via receipt of the radio frequency signal; and at least one signal processor adapted to provide three-dimensional data comprising a position, an orientation, an acceleration, and/or a velocity of the object in a three-dimensional space by processing a collected data set comprising the motion data, the direction of arrival data, the amplitude data, and the phase data.

Also described herein are systems and methods for monitoring the motion of a target platform, wherein said target platform implements the use of radio frequency transmissions. In certain embodiments, the method comprises:

intercepting motion data of a target platform via a radio frequency transmission generated by said target platform, wherein receiving the motion data via the radio frequency transmission further provides direction of arrival data, amplitude data, and phase data from the radio frequency transmission; and processing a collected data set comprising the motion data, the direction of arrival data, the amplitude data, and the phase data, wherein said processing provides three-dimensional data comprising a position, an orientation, an acceleration, and/or a velocity of the target platform in a three-dimensional space.

The "object" for which the methods and systems described herein may apply include any object that is in motion, or is capable of being set in motion. In certain embodiments, the object comprises a vehicle. Exemplary vehicles include, but are not limited to, civilian or military vehicles, watercraft, or aircraft. In certain embodiments, the object comprises an animal, such as a wild animal, pet, or a human. In certain embodiments, the object may comprise two or more segments. As used herein, the term "segment" generally refers to a portion of an object that is adapted to move in a three-dimensional space in a manner that may be unique and independent from other object segment(s). In addition, two or more segments may be linked together in a manner that allows for the unique and independent motion of each segment. Exemplary segments include, but are not limited to, the body parts of an animal, such as upper and lower limbs. In certain embodiments, the segments are selected from upper and lower arms, and upper and lower legs, which are linked by elbows and knees, respectively. In certain embodiments, the object comprises two or more segments. In certain embodiments, at least one motion sensor tag is disposed on each segment, wherein motion data related to each segment is collected.

In certain embodiments, the methods and systems described herein may be implemented to track or monitor the movement of a target platform that generates motion data about the target platform via a radio frequency transmission. Exemplary target platforms include any movable object that implements radio frequency transmissions, such as watercraft or aircraft, including an unmanned aerial vehicle (UAV or "drone"). In certain embodiments, the method may be employed to monitor the target platform for collision sense and avoidance. In certain embodiments, the radio frequency transmission employed with a target platform such as a UAV system may comprise a communications downlink signal or other radio frequency signal emanating from the UAV, thereby avoiding the need to position a motion sensor tag on the UAV or to illuminate the UAV with a monostatic radar and, thus, possibly reducing the UAV's power requirements.

In certain embodiments, the methods and systems described herein may have particular use in virtual reality gaming or military training exercises. For instance, motion sensor tags (or simply "tag") may be disposed on one or more limbs of a soldier to actively monitor soldiers on outdoor training exercises. Such uses may include monitoring the body position of a dismounted soldier, including prone, crouching, kneeling, and weapon handling and pointing. Similarly, motion sensor tags may be disposed on an individual for determining the position, orientation, acceleration, and/or velocity of a player, wherein such data is transferred to a remote computing device that implements the use of a virtual reality headset or goggles. In certain embodiments, the remote computing device may be connected to virtual reality gear via a wired or wireless connection, which itself may contain onboard processing capabilities for further manipulation of the data. Accordingly, in certain embodiments, the motion sensor tags may be disposed on one or more limbs of the human body, with the option of disposing one or more additional tags on a secondary object (e.g., a gun).

In certain embodiments, each motion sensor tag independently comprises an inertial measurement unit (IMU). In certain embodiments, the IMU is adapted to collect motion data from the portion of the object two which it disposed. An exemplary IMU may comprise one or more accelerometers, gyroscopes and/or magnetometers. In one non-limiting example, the IMU may collect motion data from at least one object segment, such as yaw data, pitch data, and/or roll data. Alternatively, or in addition, each motion sensor tag independently comprises a laser transmitter and a two dimensional photodiode array receiver wherein the motion data comprises direction of arrival and phase data and/or an ultrasonic sensor, wherein the motion data comprises time of flight data. In certain embodiments, each motion sensor tag further comprises at least one battery. In certain embodiments, each motion sensor tag further comprises at least one microprocessor, which may be adapted to format the motion data. In certain embodiments, each motion sensor tag further comprises the use of a local oscillator. In certain embodiments, the local oscillator is adapted to be phase-coherent with a local oscillator associated with a receiving antenna array.

In general, an IMU may generate position errors over a short period of time due to drift. The motion capture accuracy of the object (e.g., position and orientation) of the methods and systems described can be improved over that of a standalone IMU-based system by providing IMU data augmented with position revisions via a radio frequency positioning system wherein motion sensor tags containing radio frequency transmitters are worn, e.g., on the limbs of a human and/or are attached to the carried object. These tags can transmit a Continuous Wave (CW) radio frequency signal that is received by an antenna array contained in the MPU that is worn on the chest or elsewhere on the body. In certain embodiments, in addition to the motion data collected by the IMUs that is transmitted via radio frequency signals, the radio frequency network provides both Direction of Arrival (DOA) and range information between the antenna array and each motion sensor tag as determined by the received phase data and amplitude data of the baseband waveform from each tag.

In certain embodiments, the transmission of the motion data comprises the use of at least one radio transmitter. In certain embodiments, each motion sensor tag comprises at least one radio frequency transmitter for transmitting the motion data. In certain embodiments, the transmitted motion data is received in a manner that comprises the use of at least one receiving antenna, such as an antenna array. In certain embodiments, processing the collected data set comprises the use of a digital signal processor. In certain embodiments, the digital signal processor is adapted to receive the motion data, the direction of arrival data, the amplitude data, and the phase data from at least one receiving antenna, such as via a wired or wireless signal. In certain embodiments, the digital signal processor comprises a sensor fusor. In certain embodiments, the sensor fusor implements the use of a sensor fusor algorithm that is adapted to combine the motion data, direction of arrival data, phase data, and/or amplitude data.

In certain embodiments, the system and methods described herein further comprise the use of a main processor unit. The main processor unit may be adapted to process the motion data received from one or more of the motion sensor tags. In certain embodiments, the digital signal processor is contained in a main processor unit. In certain embodiments, the main processor unit is powered by at least one battery, such as a rechargeable lithium ion battery. The main processor unit may further comprise a connection to a remote computing device, which may be implemented to transmit the three-dimensional data comprising a position, orientation, acceleration, and/or velocity of the object in a three-dimensional space to a remote computing device. In certain embodiments, the connection may comprise a wireless connection, such as a wireless antenna, having 3G, 4G, and/or WiFi capabilities.

In certain embodiments, the collected data set for processing may further comprise predetermined constraint data. As used herein, "predetermined constraint data" comprises a predetermined limitation, such as an algorithmic limitation, that is not generated in real time and is employed to define parameters around motion data collected for processing. Predetermined constraint data may be applied in an effort to correct drift and/or noise errors that may be associated with the collection of motion data from an object. Thus, in certain embodiments, predetermined constraint data is not generated by one or more of the motion sensor tags.

In certain embodiments, the constraint may comprise predetermined biomechanical constraint data, wherein certain predetermined biomechanical limitations are applied to an object like the human body. For example, in certain embodiments, motion sensor tag readings may be correlated according to a biomechanical model that allows for a certain degree of flexibility (e.g., laxity) in the joints and, thus, provides for different biomechanical characteristics for various joint types, such as biomechanical constrains defined for joints such as the knee and the shoulder. Therefore, a predetermined biomechanical constraint model, such as predetermined joint constraint data, may allow for a higher level of accuracy in estimating body motion. Predetermined biomechanical constraint data, such as joint flexibility data, may be derived from sources known to those of ordinary skill, such as data relevant to various joint types described in Zatsiorsky, "Kinematics of Human Motion," Human Kinetics (1998), which is incorporated herein by reference in its entirety for all purposes.

However, in certain embodiments, the methods and systems described herein do not implement the use of predetermined constraint data. Without being bound to any particular theory, in certain embodiments, Applicant has surprisingly discovered that processing a collected data set containing, or consisting essentially of, motion data, direction of arrival data, amplitude data, and phase data is sufficient for providing detailed and accurate three-dimensional data comprising the position, orientation, acceleration, and/or velocity of an object in a three-dimensional space. Thus, predetermined constraint data may not be necessary to provide accurate three-dimensional data. Accordingly, in certain embodiments, the collected data set does not comprise predetermined constraint data. In certain embodiments, the collected data set does not comprise predetermined joint constraint data. In certain embodiments, the collected data set does not comprise predetermined joint flexibility data.

In certain embodiments, the method and systems described herein implement the use of external contact data. As used herein, "external contact data" comprises an intersection of the mesh model of an object with a mesh model of a space in which the object exists, which may be implemented to limit any boundless integration errors that may be found in motion data derived from the object's movement in the space. In some embodiments, external contact data comprises data such as position, velocity, and/or acceleration of the object and/or one or more of its segments. In some embodiments, external contact data is predetermined and is based on prior data points that are not collected in real time, i.e., not collected during the processing of the collected data set. Thus, in certain embodiments, external contact data is predetermined data that may be collected by one or more of the motion sensor tags. In other embodiments, the external contact data is collected by contact sensors.

However, in certain embodiments, the methods and systems described herein do not implement the use of external contact data. Without being bound to any particular theory, in certain embodiments, Applicant has surprisingly discovered that processing a collected data set containing, or consisting essentially of, motion data, direction of arrival data, amplitude data, and phase data, is sufficient for providing detailed and accurate three-dimensional data comprising the position, orientation, acceleration, and/or velocity of an object in a three-dimensional space. Thus, external contact data may not be necessary to provide accurate three-dimensional data. Accordingly, in certain embodiments, the collected data set does not comprise external contact data.

The following embodiments are exemplary only and should not be viewed as limiting the scope of the present disclosure.

FIG. 1 provides a front view of an exemplary motion sensor system, comprising motion sensor tags, including motion sensor tag 100, attached to segments (limbs) of an object (human body), which include an IMU and radio frequency transmitter. Motion sensor tag 100 may be disposed on the body via any suitable means known to those of skill in the art, including adhesives and patches. Motion sensor tag 100 may also be attached to clothing or inserted into pockets in cloths or uniforms, or attached by velcro. MPU 200 may be disposed on the torso of the body. MPU 200 comprises an antenna array that may be worn on the human's chest or any other location that provides accurate position, velocity and acceleration information that the human is being subjected to. Motion sensor tag 100, if attached to a carried object, also measures the orientation of the carried object, allowing precise handling and/or pointing accuracy to be derived. Motion sensor data of the object being measured is displayed on remote computing device 300.

Figure 2:
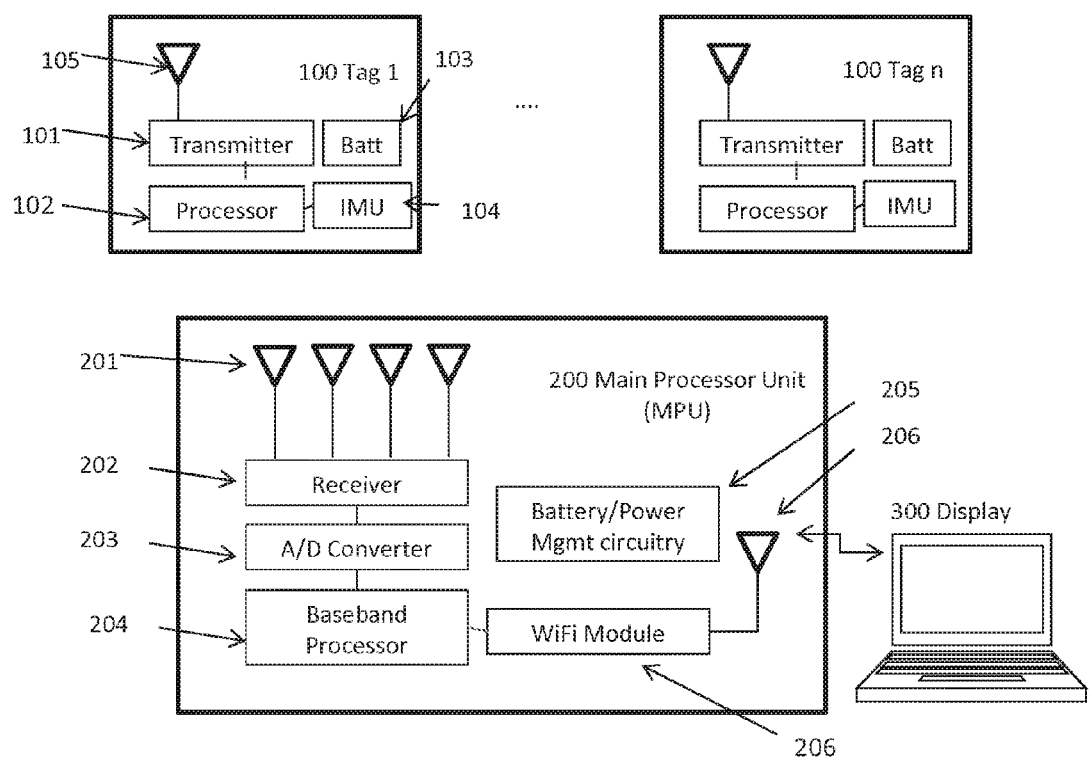
FIG. 2 is a block diagram illustrating an exemplary motion sensor system.

FIG. 2 is a block diagram illustrating an exemplary motion sensor system, comprising motion sensor tags (motion sensor tag 100 (tag 1) and tag n), MPU 200, and remote computing device 300. Motion sensor tag 100 contains radio frequency transmitter 101, which itself further comprises radio frequency antenna 105. Motion sensor tag 100 further contains microprocessor 102 and IMU 104. MPU 200 contains receiving antenna array 201, which is associated with receiver 202, A/D converter 203, baseband processor 204, battery and battery management circuitry 205 and the WiFi communications module 206

Figure 3:
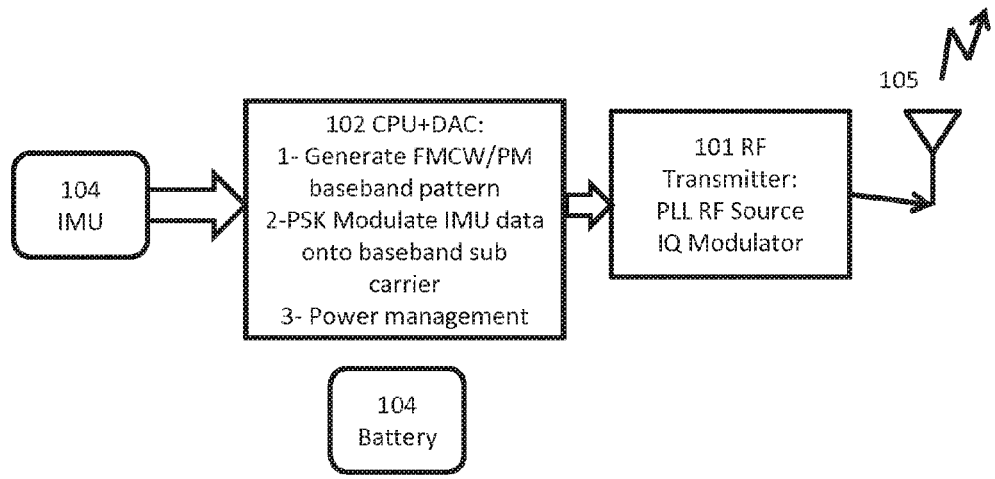
FIG. 3 is a block diagram illustrating the components of an exemplary motion sensor tag.

FIG. 3 is a block diagram illustrating signal flow and processing within a motion sensor tag. The IMU accelerometer, gyroscope and magnetometer data may be transferred via a serial data bus, e.g. Serial Peripheral Interface (SPI) or Inter IC (I2C) to the Digital to Analog Converter (DAC) and/or directly to microprocessor 102. The microprocessor generates the baseband waveform and multiplexes the collected IMU motion data onto a subcarrier. Power management is also performed by the microprocessor. The baseband motion data is then upconverted and transmitted by radio frequency transmitter 101. All of the motion sensor tag electronics are powered by rechargeable battery 104.

Figure 4:
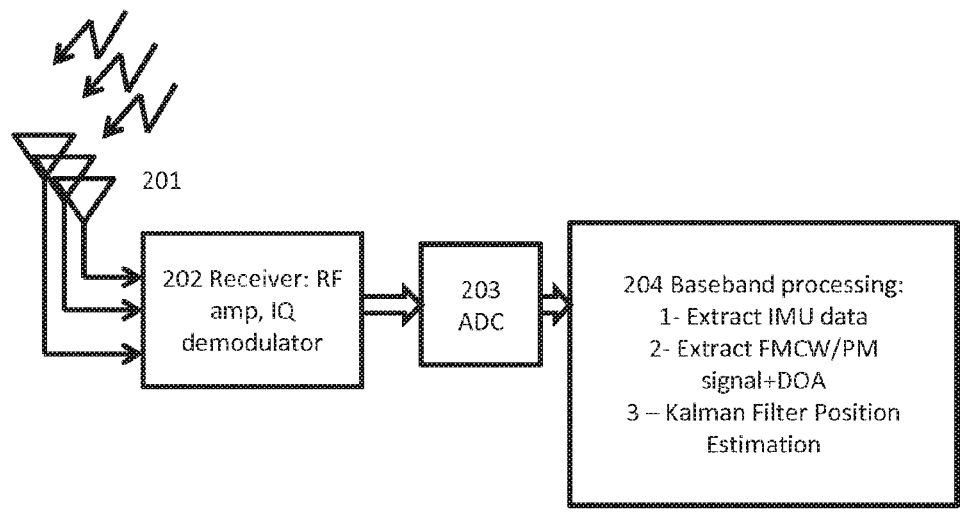
FIG. 4 is a block diagram illustrating the components of an exemplary receiving antenna, receiver, and main processor unit.
Figure 5:
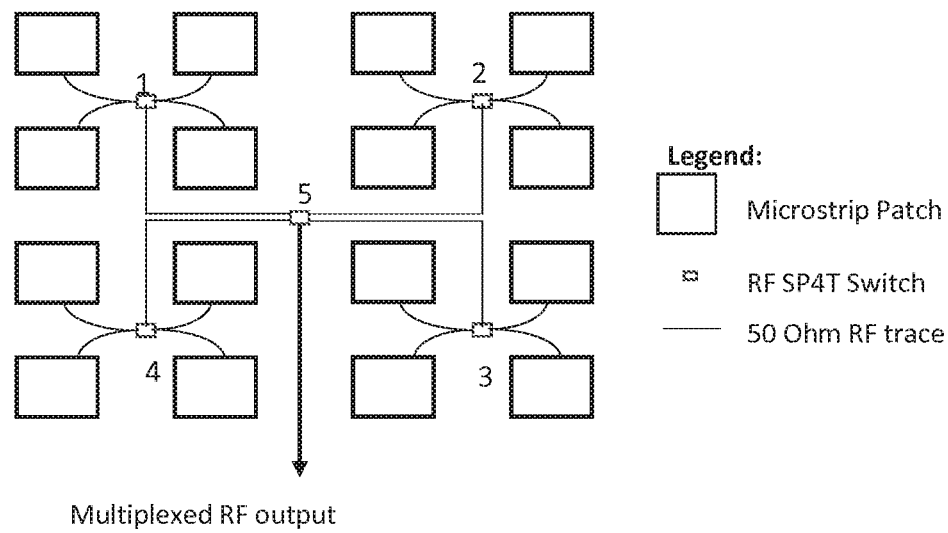
FIG. 5 is a front view of an exemplary antenna array.
Figure 6:
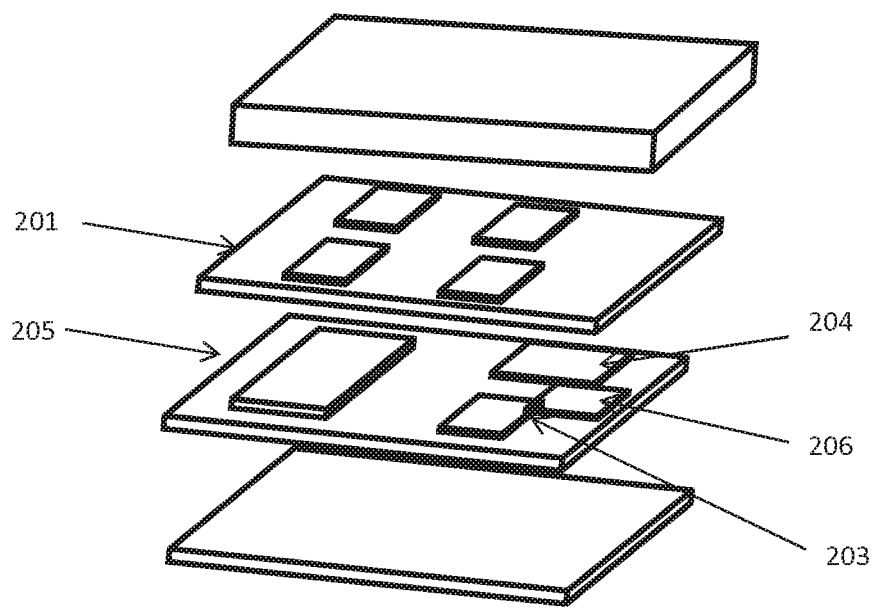
FIG. 6 is an exploded perspective view of an exemplary main processor unit.

FIG. 4 is a block diagram illustrating the MPU 200. Antenna array 201 (which may be a phased array and, optionally, a switched phased array antenna) receives the radio frequency signals from each motion sensor on each of the antenna elements. The array may be a uniform rectangular array or a uniform circular array. In one embodiment, the array may be worn on the chest, while in another embodiment, the array may be embedded in a helmet brim to provide an increased field of view. The array may be antenna array 201 as shown in FIG. 5, where each antenna element is sequentially sampled and processed by a single coherent receiver to reduce the hardware cost. FIG. 5 demonstrates that exemplary planar switched antenna array 201 comprises four switched 4 element sub-arrays that are further switched amongst the four sub-arrays to form a 16 element array. FIG. 6 is a perspective exploded view of an exemplary MPU, showing the MPU housing containing the planar switched antenna array 201 and receiver 202 on a single board, the main processor board containing A/D converter 203 and baseband processor 204, battery and battery management circuitry 205 and WiFi communications module 206.

Figure 7:
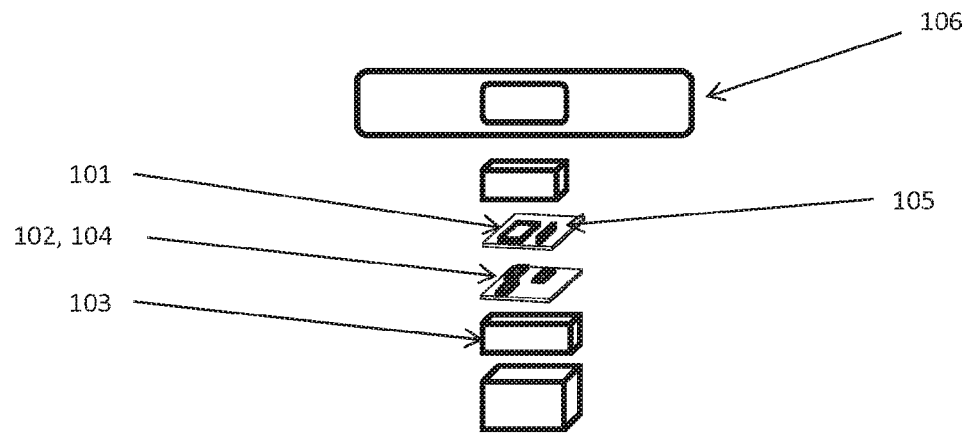
FIG. 7 is an exploded perspective view of an exemplary motion sensor tag.
Figure 9:
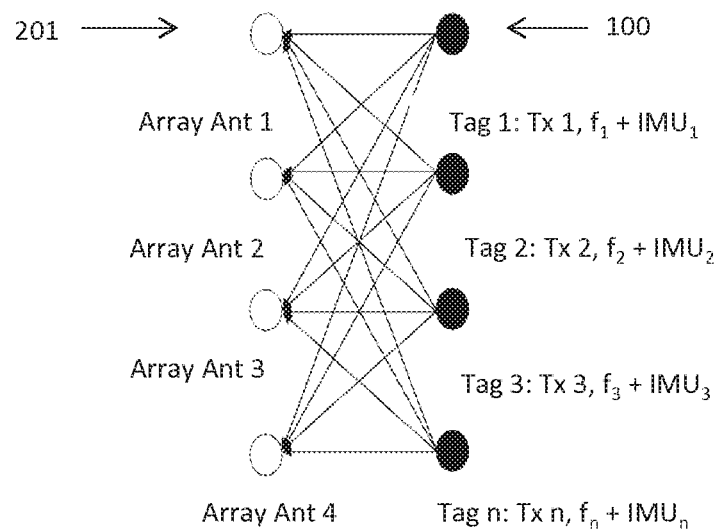
FIG. 9 illustrates the sub-operation of an exemplary radio frequency (RF) network diagram depicting ray traces from the motion sensor tags transmitted to an antenna array.

FIG. 7 is an exploded upper perspective view of motion sensor tag 100 depicting radio frequency transmitter 101 which includes radio frequency antenna 105, integrated with microprocessor 102, IMU 104 and rechargeable battery 103. In operation, motion sensor tag 100 collects and processes collected motion data, and transmits the motion data via the radio frequency transmitter to receiving antenna array 201 and forwards the processed information via a WiFi connection between the MPU and the remote computing device 300 that displays the motion data on a graphical user interface (GUI). FIG. 9 illustrates a sub-operation of the radio frequency network, depicting ray traces from the motion sensor tags 100 to receiving antenna array 201 for DOA and range determination.

Figure 10:
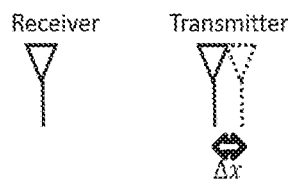
FIG. 10 demonstrates an exemplary phase modulation effect of the relative motion of the transmitting motion sensor tag antenna toward or away from a receiving antenna.

FIG. 10 shows the phase modulation effect of the relative motion of the radio frequency antenna toward or away from the receiving antenna. A change in axial distance will result in a change in the RF phase of the received signal which can be mathematically represented as follow:

$$\Delta\theta = \frac{2\pi}{\lambda}\Delta x$$

where $\Delta x$ is the axial displacement, $\lambda$ is the wavelength of the RF signal and $\Delta\theta$ is the shift in RF phase due to axial displacement. $\Delta\theta$ is measured in baseband after downconversion given the standard representation of complex baseband model in communication systems:

$$s(t)=e^{-j\Delta\theta}$$

where s(t) is the time domain complex baseband signal comprising of in-phase (I) and quadrature (Q) components.

Figure 11:
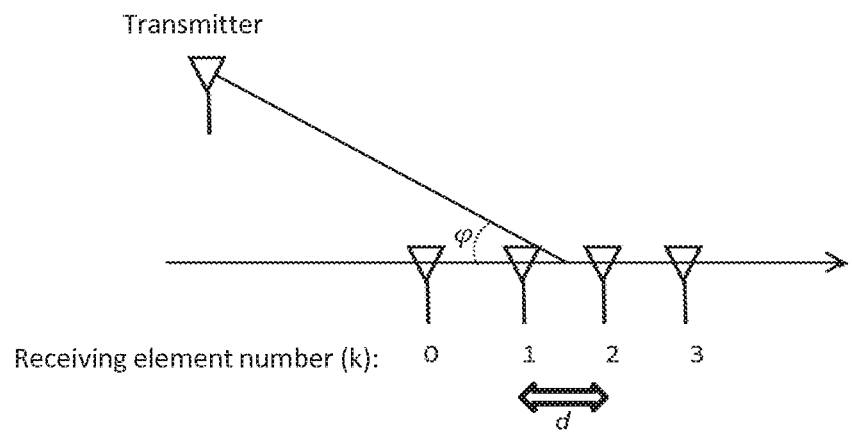
FIG. 11 demonstrates an exemplary linear receiving antenna array and a single transmitter element as a representation of the cross-section of the uniform rectangular array in one dimension.

FIG. 11 shows a linear receiver antenna array and a single transmitter element. Each receiver element will receive the signal at a slightly different phase due to the variation in distance. The DOA is defined in the figure. The complex baseband model of the received signal from element k is calculated as:

$$s_k(t) = e^{-j[\Delta\theta + \frac{2\pi}{\lambda}kd\cos(\varphi)]}$$

where d is the element spacing, k is the element number and $\varphi$ is the DOA.

Figure 12:
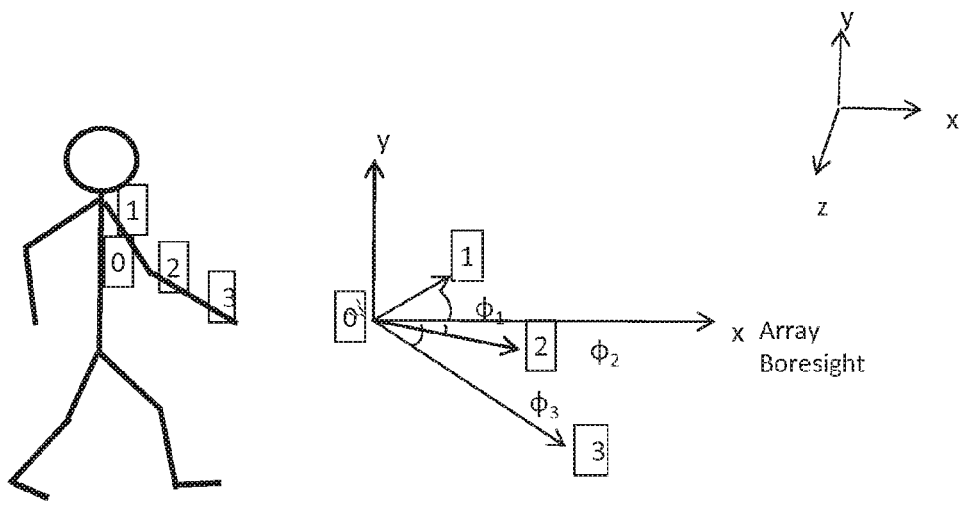
FIGS. 12 and 13 demonstrate angular geometries of motion sensor tags attached to the arm (wrist, elbow, shoulder) and the leg (ankle, knee, hip) relative to a receiving antenna array for the determination of direction of arrival data for each tag.
Figure 13:
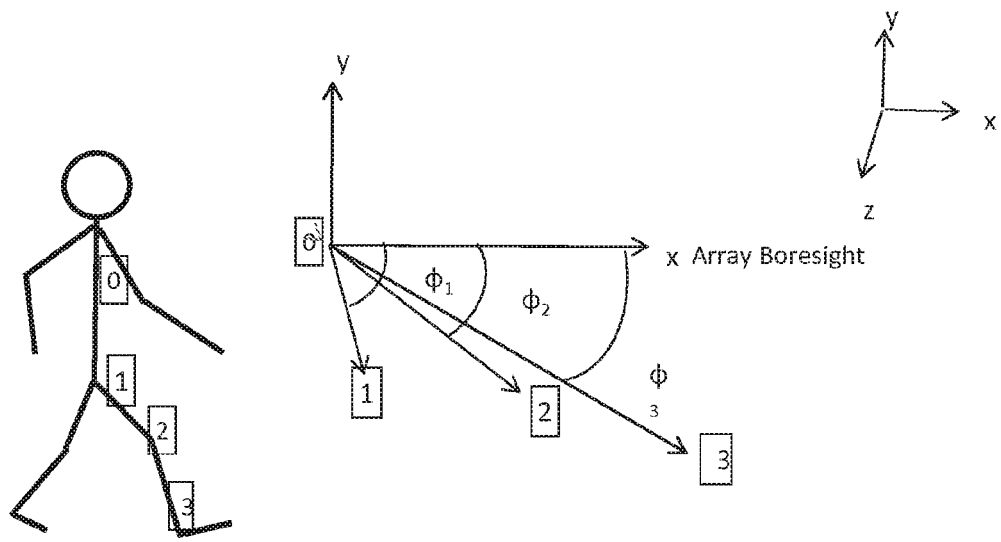

FIGS. 12 and 13 depict the angular geometries of the motion sensor tags attached to the arm (wrist, elbow, shoulder) and the leg (ankle, knee, hip) relative to the receiving antenna array for the determination of the DOA for each tag.

The receiving antenna will intercept the radio frequency signal from the plurality of motion sensor tags and will use that information to recover the position of each individual tag. In certain embodiments, high resolution DOA determination methods, including published techniques such as Multiple Signal Classification (MUSIC) and Minimum Variance Distortionless Response (MVDR) algorithms, can be used to locate the DOA for radio frequency signals received from each individual radio frequency transmitter with angular spatial resolution capabilities of less than a degree. The radio frequency signal that each radio frequency antenna transmits is modulated by the motion of the object and such motion results in the correlated modulation of the baseband phase of the received signal, and upon demodulation by MPU 200, the received signal can be used to recover distance from the motion sensor tag. Additionally, motion data generated by the IMU will be recovered from each element after de-multiplexing the received signals in antenna array 201. The position data from the IMU and that obtained from the DOA and phase demodulation approach will be processed by a Kalman filter for generating an accurate acceleration, velocity and position from the combination of signals produced by the motion sensor tags. In certain embodiments, should there be any blockage of the radio frequency signal, the system will rely on the IMU motion data until the radio frequency signal is recovered, at which time position revisions derived from DOA data, phase data, and amplitude data will be passed to the Kalman filter.

In certain embodiments, having antenna array 201 mounted on a moving body such as the human chest can potentially result in erroneous readings due to the natural tendency for the chest to move with each breath. In order to compensate for this, Applicant has implemented a novel method to account for this variance. When the chest is still, the distance reported to each motion sensor tag can be plotted and graphed accurately on a computer display. However when the chest is moving, the calculated distance to each tag will fluctuate with each chest movement. In order to cancel out this movement, in certain embodiments, the system will measure the distance to each motion sensor tag, but use that distance as a reference to each other tag. Since antenna array 201 will have the same displacement relative to each tag, the distance reported between each motion sensor tag will remain the same. Using this distance between each motion sensor tag, an accurate reconstruction of the dynamic positions of the user's extremities can be mapped on a display. Signal processing methods such as Independent Component Analysis (ICA) can be used to distinguish the chest movement from the motion sensor tag movement. In certain embodiments, this method will work for any movement of the antenna array and will provide for accurate and stable measurements.

Instead of relying on rather weak backscatter in radar, certain embodiments of the systems described herein rely on the actual received signal from the motion sensor tag, which is significantly stronger than a backscatter signal. Alternatively, in the case of determining the position of an approaching aircraft or UAV object, the RF signals emanating from the target may be used to determine the position of the object. In addition, using motion sensor tag 100 helps positive identification of the body part or the carried object it is attached to. Each tag generates a low power modulated Continuous Wave (CW) signal at either 2.4 GHz, 5.8 GHz or potentially at other frequency bands. This radio frequency signal is received at a multi-element planar patch antenna array worn on the subject's chest or elsewhere on the body or on the UAV platform. The antenna array permits the measurement of the DOA of the received signal by comparing the phase difference between adjacent antenna elements. To reduce the complexity and cost of the array, in certain embodiments, a switched antenna architecture will multiplex the individual array antenna elements into a single RF feed, thus requiring only a single channel receiver to demodulate the entire antenna array. The planar antenna array may be etched onto a printed circuit board (PCB) and lends itself well to a compact form factor. The antenna feed network may also be etched onto the PCB. Additionally, the RF front-end may be placed on the same antenna board and removes the need for any coaxial cables and connections.

With reference to the figures, the radio frequency signal is filtered and downconverted to baseband using surface mount technology (SMT) components and chipsets in receiver 202. Digital signal processor 204 comprises a baseband processor that hosts the digital signal processing (DSP) code that processes the received waveform from each motion sensor tag. In addition to providing the DOA for each motion sensor tag, the DSP algorithm determines the instantaneous range to each tag by comparing the modulated phase of the received waveform to the phase of the reference signal generated by a Local Oscillator (LO).

IMU 104, microprocessor 102, radio frequency transmitter 101, rechargeable battery 103 and radio frequency antenna 105 are packaged into the body-worn motion sensor tag 100. The waterproof and shockproof tags contain the antenna and radio frequency transmitter that broadcasts a modulated CW waveform at a frequency unique to each motion sensor tag. In this way, each tag can be uniquely identified by its frequency (e. g. Tag 1 transmits at frequency $f_1$, tag 2 at frequency $f_2$, etc). The IMU data output may also transmitted on a subcarrier for each tag. See FIG. 9.

As previously noted, each motion sensor tag may be attached at various locations on the body and incorporates a 9 Degree of Freedom (DOF) Micro-Electro-Mechanical Systems (MEMS) IMU, combined with a modulated RF positioning sensor that transmits a Continuous Wave (CW) radio frequency signal. The 9 DOF MEMS IMU may contain a 3-axis accelerometer, 3-axis gyroscope and 3-axis magnetometer. This radio frequency signal may be used for calculating DOA and range information from each tag to the body worn receiver array. This exemplary hybrid combination may provide for a robust solution that leverages the performance advantages of each technology, thus providing a highly accurate and robust kinematics measurement and tracking capability for the motion capture system. Given that some IMUs are prone to position drift, compensation for these errors can be accounted for by incorporating RF signal-generated data (e.g., DOA, phase, and amplitude) into the collected data set to be processed.

In certain embodiments, motion sensor tag 100 comprises, inter alia, microprocessor 102 and a small form factor chip or radio frequency antenna 105 (e.g., PCB trace antenna). In certain embodiments, microprocessor 102 comprises a central processing unit (CPU) and a Digital-to-Analog Converter (DAC). The CPU gathers information from the IMU, combines it with its internally generated phase modulated (PM) baseband signal, and sends it to the radio frequency up-converter for transmission. The internally-generated radio frequency carrier signal is also used for radio frequency position recovery by demodulating the baseband phase of the received signal at antenna array 201. In certain embodiments, the IMU motion data is Binary Phase Shift Keyed (BPSK) or Frequency Shift Keyed (FSK) modulated onto a subcarrier at the $f_{subcarrier}$ frequency. The baseband phase modulated signal and the BPSK/FSK modulated IMU motion data are then added and sent to the RF circuitry for up-conversion and transmission. The subcarrier frequency may be selected such that it will not interfere with the PM baseband information. Alternatively, the IMU data is BPSK or FSK modulated onto the main carrier and a separate sub-carrier is used to convey phase information for position recovery.

Figure 8:
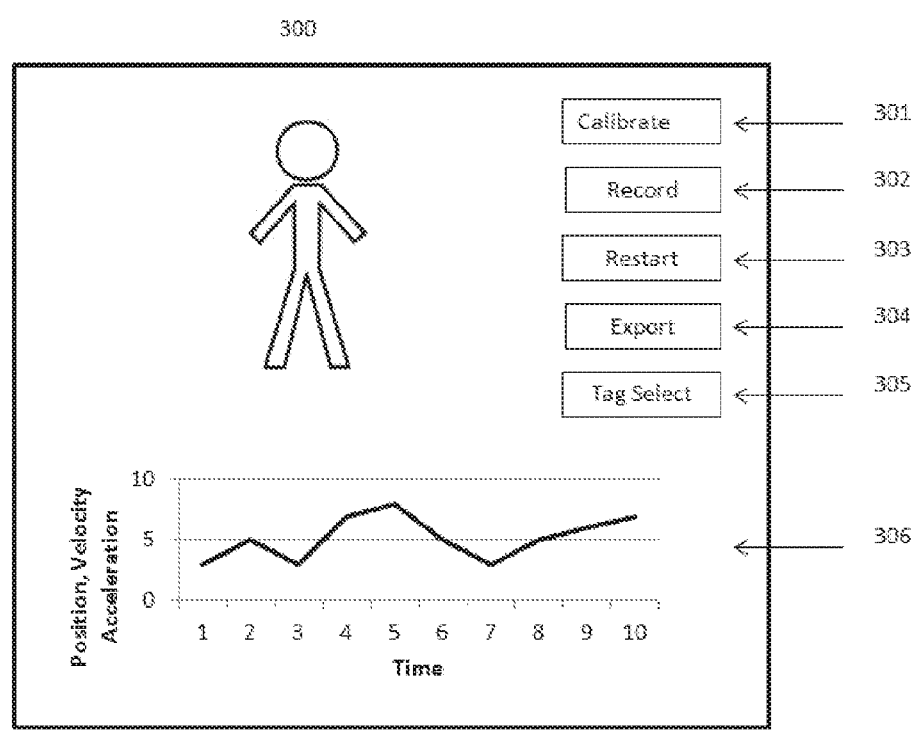
FIG. 8 is an exemplary general user interface (GUI) for displaying motion data after processing.

FIG. 8 represents a GUI screenshot showing a representative reconstructed skeleton image and user selectable buttons that select the data display. Selectable button functions include calibration 301, record 302, re-start 303, export 304 and tag select 305. Main Display Window 300: This window will show the motion sensor tags representing the user. Data will be displayed as 3-dimensional vectors. This will allow the window to be rotated to any angle to show the user from different positions. Adjacent segment angles will also be displayed. Tags attached to the users' carried object will also be displayed in real time. Data will be updated at a rate of 100 Hz to provide smooth and accurate visualization.

Calibrate 301: This button may be used to initialize the tags. The user will stand in a fixed position for a short period of time while the software determines which sensor tags are where. During this period lines will be drawn between the tags in the main display window creating a rudimentary wireframe skeleton representing the user.

Record 302: Clicking this button may be used to start the recording process. This process will record all data that is represented by the GUI. This will include the acceleration, velocity, and relative position of each tag. The data will be saved as a. Txt or. Csv file locally.

Restart 303: The restart button may be used to restart the recording process, saving over previous data (with appropriate user prompts and a file over-write warning).

Export 304: Export may be used to save all recorded data as a. Txt or. Csv file. This data can be directly imported into Excel or Matlab for post processing.

Tag Select 305: This button may be used to open up a dropdown menu that will allow individual tag data to be selected and displayed in the graphing region.

Graph 306: A graph representing the tag selected from the Tag Select button may be displayed here. The graph will visually show the acceleration, velocity or position of each tag updated in real time. Data from all tags will be saved locally using the Export feature for later post processing.

The GUI display can be located in proximity to the subject(s) being monitored or could be located at a remote location.

The antenna array, which may be located in the MPU, can be incorporated into a headgear similar to a hat or helmet, where the hat or helmet brim contains a uniform circular antenna array that provides a more optimal field of view of the tags. Alternatively, the MPU signal processor and battery can be located elsewhere on the body to minimize the added weight to the helmet. This variation avoids the situation where the motion sensor tags are shadowed by the body when the antenna array is worn on the chest.

The operation of the embodiments described herein may allow user to attach tags containing the IMU, transmitter electronics and battery, to the wrist, elbow, shoulder, hip, knee, ankle and head. The MPU may be worn on the chest or possibly integrated into a helmet. Upon activation of the motion sensor tags, the MPU calibrates the system and processes the radio frequency signal received from each tag and determines the acceleration, velocity and position of each tag. This information is then transmitted to an external computer that displays the user's body position, velocity and acceleration where tags are attached. Such a system, as described, may permit the user to roam freely without being tethered to a position measurement system, or restricted to remain within the field of view of a camera or sensor based system, as is frequently the case with current game systems.

What has been described and illustrated herein is an embodiment of the invention along with some of its variations. The terms, descriptions and figures used herein are set forth by way of illustration only and are not meant as limitations. Those skilled in the art will recognize that many variations are possible within the spirit and scope of the invention in which all terms are meant in their broadest, reasonable sense unless otherwise indicated. Any headings utilized within the description are for convenience only and have no legal or limiting effect.

The invention claimed is:

1. A system comprising:
   a plurality of motion sensor tags adapted to collect motion data from an object;
   at least one radio frequency transmitter adapted to transmit the motion data via a radio frequency signal;
   at least one phased antenna array adapted to receive the motion data from the radio frequency signal, wherein receipt of the motion data further provides direction of arrival data, amplitude data, and/or phase data; and
   at least one signal processor adapted to provide three-dimensional data comprising a position, an orientation, an acceleration, and/or a velocity of the object in a three-dimensional space by processing a collected data set, wherein the collected data set comprises the motion data, and the direction of arrival data, the amplitude data, and/or the phase data, and wherein the collected data set optionally further comprises time of flight data.

2. The system according to claim 1, further comprising at least one ultrasonic sensor.

3. The system according to 1, wherein the object comprises a human.

4. The system according to claim 1, wherein the object comprises two or more segments, and wherein at least two of the segments are each adapted to receive one or more of the motion sensor tags.

5. The system according to claim 4, wherein the two or more segments comprise body segments of an animal.

6. The system according to claim 3, wherein the body segments are selected from at least one of upper arms, lower arms, upper legs, lower legs, elbows, or knees.

7. The system according to 1, wherein each motion sensor tag comprises an inertial measurement unit.

8. The system according to claim 7, wherein the motion data comprises yaw data, pitch data, and/or roll data.

9. The system according to claim 7, wherein each motion sensor tag comprises at least one radio frequency transmitter for transmitting the motion data.

10. The system according to claim 9, wherein each motion sensor tag comprises a microprocessor.

11. The system according to claim 10, wherein the microprocessor is adapted to format the motion data.

12. The system according to claim 11, wherein the microprocessor is adapted to generate a baseband waveform of the motion data, and upconvert the motion data to the at least one radio frequency transmitter.

13. The system according to claim 1, wherein the at least one phased antenna array is connected to a receiver.

14. The system according to claim 1, further comprising a digital signal processor contained in a main processor unit.

15. The system according to claim 14, wherein the main processor unit further comprises a wireless connection.

16. The system according to claim 15, wherein the main processor unit is adapted to transmit the three-dimensional data via the wireless connection to a remote computing device.

17. The system according to claim 16, wherein the remote computing device is adapted to display the three-dimensional data.

18. The system according to claim 17, wherein the remote computing device comprises a virtual reality headset or virtual reality goggles.

19. The system according to claim 1, wherein the collected data set further comprises predetermined constraint data.

20. The system according to claim 1, wherein the antenna array comprises a planar switched antenna array.

21. The system according to claim 20, further comprising a Kalman filter.

* * * * *